(12) United States Patent
Redko et al.

(10) Patent No.: US 8,284,247 B2
(45) Date of Patent: Oct. 9, 2012

(54) METHOD AND APPARATUS FOR DETECTING AND INSPECTING THROUGH-PENETRATING DEFECTS IN FOILS AND FILMS

(75) Inventors: Volodymyr I Redko, Coral Springs, FL (US); Volodymyr S Khandetskyy, Dnipropetrovsk (UA); Elena M. Shembel, Coral Springs, FL (US)

(73) Assignee: Enerize Corporation, Coral Springs, FL (US)

( * ) Notice: Subject to any disclaimer, the term of this patent is extended or adjusted under 35 U.S.C. 154(b) by 686 days.

(21) Appl. No.: 12/378,330

(22) Filed: Feb. 14, 2009

(65) Prior Publication Data

US 2009/0207244 A1    Aug. 20, 2009

Related U.S. Application Data

(60) Provisional application No. 61/065,972, filed on Feb. 15, 2008.

(51) Int. Cl.
*H04N 7/18* (2006.01)
*G01N 21/00* (2006.01)
(52) U.S. Cl. ........................... 348/88; 356/237.1
(58) Field of Classification Search ............ 348/88
See application file for complete search history.

(56) References Cited

U.S. PATENT DOCUMENTS

| | | | | |
|---|---|---|---|---|
| 5,696,591 A | * | 12/1997 | Bilhorn et al. | 356/429 |
| 5,732,529 A | * | 3/1998 | Dey et al. | 53/389.2 |
| 7,692,144 B2 | * | 4/2010 | Watanabe et al. | 250/307 |
| 2002/0008093 A1 | * | 1/2002 | Ukita et al. | 219/121.72 |
| 2008/0158396 A1 | * | 7/2008 | Fainstain et al. | 348/246 |
| 2009/0297019 A1 | * | 12/2009 | Zafar et al. | 382/145 |

* cited by examiner

*Primary Examiner* — Aaron Strange
*Assistant Examiner* — James Edwards
(74) *Attorney, Agent, or Firm* — Morgan Lewis & Bockius LLP; Richard F. Trecartin

(57) ABSTRACT

The present invention is a method and apparatus for optical detection and size evaluation of through-penetrating defects such as pinholes in moving foil or film. The invention comprises the installation of at least one image capture device at a first given distance over the moving foil surface, placement of at least one elongated light source comprising an infinite number of point-sources that are not in phase, and are emitting light independently from one another under the foil, periodic automatic computer-controlled image capture of the foil surface with image capture devices, automatic transmission of the image captured by each device to a control computer, and processing of the transmitted image data to detect of defect light spot, followed by determination of generalized index of its initial image. This generalize index value is equal to the brightness averaged within the spot multiplied by the area of the spot. The invention further includes reporting the presence of a through-penetrating defect when the generalized index value exceeds a preset threshold. characteristics of the defect spots.

14 Claims, 4 Drawing Sheets

METHOD AND APPARATUS FOR DETECTING AND INSPECTING THROUGH-PENETRATING DEFECTS IN FOILS AND FILMS

CROSS-REFERENCE TO RELATED APPLICATIONS

U.S. Provisional Patent Application No. 61/065,972, filed Feb. 15, 2008

FEDERALLY SPONSORED RESEARCH

None

SEQUENCE LISTING

None

FIELD OF THE INVENTION

This invention relates to optical non-destructive testing for the detection of defects that penetrate through metal foils or opaque film test articles, and especially for detection of penetrating defects or pinholes and evaluation of defect size in moving foil test articles.

BACKGROUND OF THE INVENTION

Optical methods of non-destructive quality control are used for examination of surface relief and for flaw detection in a variety of articles. In these inspection methods light reflected from article's surface, or light that has come through a defect that penetrates completely through the test article (penetrating defect) is registered by a photo-detector and used as the information signal. Existing methods for detection of defects that penetrate through foils and films have several disadvantages.

The method detection of defects in a circular or spiral diffraction grating", a device detecting topographic defects in the process of optic control of round and spiral tracks on article's surface is proposed in literature. These tracks set a diffraction grating analogous to those existing on a video-disk or an optical recording disk. Irregularity of spatial track distribution is registered by characteristics of diffraction reflection from surface, reflection being observed by means of a TV camera or a monitor.

In the literature the apparatus for defect inspection in an object having a periodic pattern is considered. This apparatus includes a system which illuminates the object with parallel light in a direction given by the first pre-set inclination angle relative to the object's surface being inspected. A sensitive cell uses an objective. Information on defects is obtained through analysis of object's image. Mutual positioning between illumination direction and image registration direction is adjusted based on diffraction angle which is determined using image period and wavelength of illumination light. Sum of aperture angle of illumination light and aperture angle of reception objective is set to a lesser value than the diffraction angle.

Other method and apparatus for detection of fine defects with high resolution of an optical image of such defects is also considered in literature. Difference achieved in contrasting image details is greater than fine lines of a semi-conductor device image. Apparatus includes a sample-mounting device, an illuminating apparatus and one detecting the reflected image, a display for optic image registration, device for adjusting parameters of the illuminating and the detecting apparatuses, a device for saving data of the images being compared and a device pointing out defects by comparing the registered and the saved optical image.

The device for detecting defects through control of light reflection off the substrate covered with transparent coating is known. The device includes polychromatic spotlight whose light beam is directed at the observed site. The direction of the light beam makes an angle greater than $\pi-\beta$, where $\beta$ is the Brewster flat-surface angle. The device also contains a registration apparatus whose optic axis is located in the same plane with the light beam, at least the first secondary source of monochromatic light, a further localized registration apparatus oriented, along with the light source, at the observed site, spotlight carrier, registration apparatus carrier and secondary source carrier, and a device for controlling carrier's relative movement in relation with the controlled surface in at least two directions parallel to this surface.

However all methods and device shortly described above-mentioned allow extract information about defects based on analysis of images obtained in the light reflected off the controlled surface. It is characteristic for detection and evaluation of geometric dimensions of non-through surface defects of the articles examined. At times, article's construction itself does not allow one to examine light passing through a transverse defect. These methods and apparatuses do not consider possibility of simultaneous defectoscopy and defectometry of a detected through defect with corresponding change in position of the light-sensitive unit and computer processing of the fixed images in real time.

At the same time, the method and apparatus that are presented in the current patent application and are based on the researches that were conducted using various registration equipment, including microscopes, has shown that in studying through the defects in thin metal foil or opaque film, the measurement methods based on registration of the light passed through a defect are distinguished by a higher sensitivity.

SUMMARY OF THE INVENTION

An objective the present invention is to carry out 100% optical non-destructive quality control of moving metal foils or opaque films, including detection of defects such as pinholes that penetrate completely through the film or foil, as well as evaluation of geometric dimensions of such defects in opaque film or foil test articles.

According to the present invention, this goal is achieved by setting up at least one image capture device such as a camera at a first set distance over the flat surface of the moving foil, by placing at least one high aspect ratio (elongated) light source under the foil, and periodically capturing images of the foil surface with one or more image capture devices.

This image capture is executed automatically under computer control, followed by automatic transmission of the image captured by each camera to the control computer and initial image processing for detection of light spots that indicate the presence of a defect. This step is followed by determination of the initial characteristics of the transmitted image.

The axis of symmetry of the objective lens of each camera or image capture device located at the first given distance over the foil test article surface and perpendicular to this surface and crosses it on the line which is parallel to foil's side edges and located equidistant from these edges. The axes of the elongated light sources located under the foil are perpendicular to side edges of the foil.

The distance between the axes of symmetry of the objectives is determined by the area of the foil-surface segment recorded by means of the camera in the working mode, and by the speed of movement of the foil and by minimal time between two consecutive automatic-mode image capture operations. The minimal time between two image capture operations is determined by the time required for the computer-controlled image capture operation and the time required for transmission of the image recorded by the camera to the computer.

Initial image-processing includes: selection of elementary image sections with brightness greater than a pre-determined level, determination of the area of the initial outline of a light spot consisting of the selected elementary sections having a common boundary, determination of a generalized index of the light spot initial image (which is equal to the average brightness within the primary outline multiplied by outline's area), and reporting the presence of a defect when the generalized index value exceeds the corresponding threshold value.

Thereafter, the generalized index of a light spot's initial image is saved. The movement of the foil is stopped. The camera that has detected a defect approaches the foil surface automatically and takes position at the second given distance from the foil. This camera moves along in the plane parallel to foil surface and stops when the defect light spot comes into focus. A secondary image of the defect light spot is then captured automatically and the image is transmitted to the computer.

Processing of the secondary image data of the defect light spot includes determination of average background brightness of the image elementary sections for which brightness is lower than the first given threshold, selection of the image elementary sections for which the brightness is higher than the second given threshold, determination of area values enclosed by the outlines of light spots consisting of the image elementary sections wherein the brightness is higher than the second given threshold and which have a common boundary, selection of the light spot with the greatest area, approximation of the selected light spot with a polynomial function raised to the third power at most, determination of the average brightness within the approximated light spot; compensation of the spot average-brightness value by subtracting the average background brightness value from it, and determination of the generalized index of the secondary image of the defect light spot by multiplying its compensated brightness by the area of the approximated outline of the spot.

The resulting value of the generalized index of the defect optical size is determined by summing up the generalized indices of the defect's initial and secondary image using respective weighting factors. The weighting factor of the generalized index of a defect image is determined by dividing the number of elementary sections that make up the given image by the total number of elementary sections that make up the initial and secondary image of the defect.

The invention further comprises a transportation means for moving the cameras along the line normal to the foil surface and in the plane parallel to foil surface, as well as means of the foil or film band movement termination, and defect-marking means have interfaces for communication with the computer.

The size or dimensions of a penetrating defect in the foil are determined by the results of comparing the value of the generalized index with calibration data. The calibration data is obtained through the above processing of images for artificial holes in the examined material whose dimensions are determined by means of microscopic measurements or by means of micrometric measurements of the size of the tool that was used to produce the artificial holes.

BRIEF DESCRIPTION OF THE DRAWINGS

Shown in the drawings are embodiments of the present invention that are presently preferred. However it is understood that the invention can be embodied in other forms without departing from the spirit or essential attributes thereof.

FIG. 2a shows form of defect; FIG. 2b shows discrete light source; FIG. 2c shows the distribution of image intensity or the replicate results for a defect image. 201 is the size of the defect square (D). 202, 203, 204 and 205 are the distances between the light sources where 202 is equal $T_0$; 203 is equal $5 T_0$; 204 is equal $D-5 T_0$; 206 is equal $D+5 T_0$.

DETAILED DESCRIPTION OF THE INVENTION

The number of cameras or image capture devices set up at the first given distance from the moving foil surface depends on the value of the foil area for which the image is recorded by the camera, taking into account the given optical conditions for the required image quality. The number of cameras is also dependant on the speed of foil movement and time necessary for the computer to prepare the camera for the next image capture.

Figure 1:
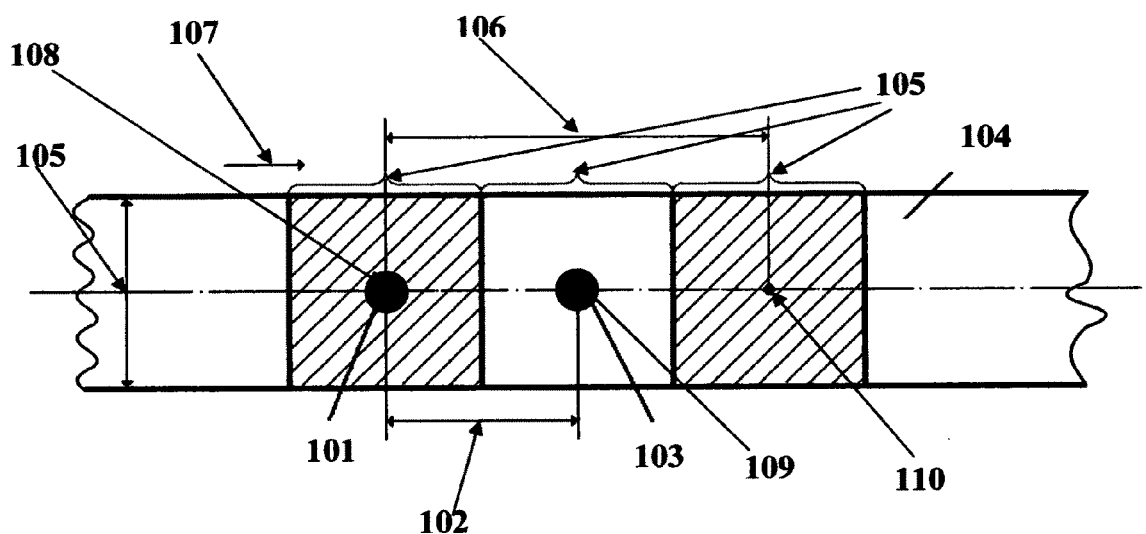
FIG. 1 represents a diagram depicting the locations of the image-producing cameras over the moving foil. 101 is the first camera; 102 is the distance ($S_{12}$) that point centered underneath camera 1 will shift during the process; 103—is the second camera; 104 is a foil; 105 is a foil area represented by a square with side a; 106 is the new distance ($S_{13}$) that point centered underneath camera 1 will shift during the process; 107 designates the foil movement speed (V); 108, 109, 110 are points centered underneath camera during the foil movement.

Referring to FIG. 1, the image recorded by the camera stretches across the entire width of the foil. FIG. 1 shows the view from above at the moving foil. The number 1 marks the position of the first camera. The image recorded by this camera includes the foil area represented by a square with side a. The V symbol on this figure designates the foil movement speed. If the total time required to capture an image and transmit it to the computer, and for the computer to prepare the camera for the next image capture is designated as τ, then the distance that point centered underneath camera 1 will shift during the time τ will equal S=Vτ. If this distance S=$S_{12}$, then in order to execute 100% optical testing (that is to capture images representing the entire surface of the moving foil), one camera will be sufficient.

However, the time required for image capture and image transmission to the computer and preparation of the camera for the next image capture amounts to several seconds for modern digital cameras. At a foil speed of 10 cm/sec the distance traveled in 3 seconds will amount to 30 sm. To obtain image of 30×30 cm foil-surface section with high resolution sufficient for detection of through-penetrating defects of up to 10 micron in size is rather difficult. This is made more difficult if speed of the foil movement is greater than 10 cm/sec, which is often the case.

If the distance traveled by the site center under camera 1 during time τ is greater than $S_{12}$, one camera will not be sufficient for achieving 100% optical quality testing. That is, one camera will not be adequate for image capture of the entire surface of the moving foil. As an example, FIG. 1 illustrates the situation when a foil section with the center located under camera 1 traveled the distance $S_{13}$ after image capture cycle time τ, so that its center is now located at point 3. In this case, in order not to skip a foil section, that is, not to leave it untested, it is necessary to set up a second camera at the distance S12 away from the first camera.

The axis of symmetry of the objective lens of each camera located at the first given distance over foil surface is perpendicular to this surface and crosses it on the line which is parallel to foil side edges and is located at the same distance away from the both edges.

An elongated (high aspect ratio) light source is located under the foil at a given distance away from its lower surface. The elongated light source is oriented in such manner that its axis is perpendicular to the direction of foil's movement. A lightproof screen is used in order to minimize sideward dispersion from the source. If two or more cameras are used for imaging of the foil surface, then, as a rule, each camera is provided with its own light source. Cameras execute periodic computer-controlled image capture along the foil surface. Images recorded by each camera are automatically transmitted to the computer. The computer compares the brightness of all elementary image sections with a given threshold value. Elementary sections with brightness greater than the threshold are selected. The configuration of the light spot of the defect is thereby determined.

The configuration appears as one consisting of the selected adjacent elementary sections, that is, sections having a common boundary. The area of defect initial light-spot image obtained is determined with the camera located the first given distance away from foil surface, that is, when the camera is far enough from this surface.

If the defect is illuminated with a parallel normal beam of light or a slanting beam, the image dimensions in the plane parallel to foil surface will theoretically match the dimensions of the defect. In the case of defect being illuminated with a divergent beam of light, a geometric μ-times increase in the size of the defect image occurs. The μ-factor depends on the distance between the light source and the foil, and on the distance between the foil and the plane of image registration. If the value of the former distance is fixed and the value of the latter increased, the μ-factor increases.

A discrete set of non-coherent point sources may be used as a light source. In this case, if images from different sources are superimposed, fields are summed up by their intensities. That is, the resulting intensity is a total of intensities of the superimposed images. A natural generalization of a discrete source-set is the case of an elongated light source, comprising an infinite number of point-sources that are not in phase, and are emitting light independently from one another.

Figure 2:
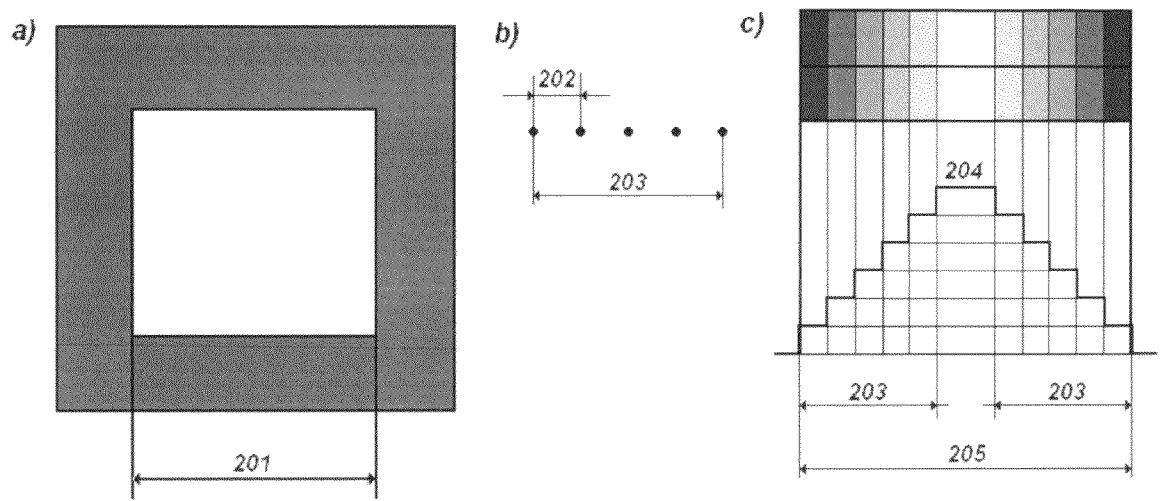
FIG. 2 shows the replicating of a through-penetrating defect's image in the form of a D×D sized square hole in foil when five discrete light sources were used.

FIG. 2 shows replicate results for an image of a defect in the form of a D×D sized square hole in foil when a discrete light source was used. The light consisted of 5 point sources located along $x_0$ axis, at a distance of $T_0$ away from one another $(D)T_0)$. The $x_0$ axis passes through the center of the square and is parallel to two of its sides. The projection of the middle point-source of the set making up a discrete light source coincides with the center of the square.

FIG. 2c shows replicate results for a defect image. It was observed that the intensity distribution changes in steps according to a linear function. Thus, a defect image is formed by registering the quantity of visible wavelength-range radiation that has passed through a defect, according to the steps described. The size of a light spot registered by a the camera depends on the distance between the light source and the foil, on the distance between the foil and the registering camera, on the relative location of the light source axis, and on the location of the axis of symmetry of the camera objective lens relative to the center of the defect. Half-tones are present in the complete image of a light spot. The image is affected by diffraction phenomena which are difficult or impossible to calculate for an irregularly shaped defect.

Image capture from a significant distance above the foil surface enables the coverage of a greater surface area, thus reducing the number of image capture cameras required both in the direction perpendicular to foil movement (for wide foil) and in the direction of movement (especially in the case of significant foil transport rate or speed of movement). But, in this case, the number of image elementary sections making up the defect light spot is significantly reduced. In some cases, for defects of about 10 microns in size, the elementary sections making up the image can be only a few pixels. As experimental results demonstrate, the brightness of the recorded light spot, other conditions being equal, depends on the size of the defect. The larger the cross-section of a through-penetrating defect, the brighter the recorded light spot.

Thus, it is advisable to combine such indices as the area of the initial outline of the recorded light spot and its brightness by introducing a generalized index equal to the averaged brightness within the initial outline multiplied by outline area. Here, the presence of a defect is reported if the value of the generalized index exceeds its threshold value. The value of the generalized index is stored in memory.

In the case that one of the cameras detects the presence of a defect penetrating through the foil, the computer generates control signals that are transmitted via communication interfaces to the unit controlling the foil movement and to the defect-marking unit. The foil movement stops. The location of the defect on the foil surface is marked. The camera that has detected the defect approaches foil surface along the normal line and is set up at the second given distance away from the surface.

Then the camera that has detected the defect starts to move in the plane parallel to the foil surface. The movement stops when the defect light spot comes into focus. The secondary image of the defect's light spot is automatically captured and transmitted to the computer.

The brightness of all the elementary sections of the image, and the co-ordinates of these sections, are indicated. Sections are selected for which the brightness is lower than that of the first given threshold t1 (see FIG. 3), and the average brightness of these sections is determined. This is the background value.

When the defect image is generated using an elongated light source, a half-shadow phenomenon occurs. This is quite widespread in practice. It should be noted that as such an elongated source grows in size, transition sections expand, which may cause significant transformation of the defect image.

If an elongated light source is placed at a certain distance from the foil having a defect, and the observation plane is at the same distance from the foil on the other side of the foil, then the beam of light rays emanating from a point along the elongated light source with X0i,Y0i co-ordinates, while passing through a small hole of δ diameter, generate a circle-like trace 2δ in diameter in the observation plane near the point X0i=X2i,Y0i=Y2i (here we replace the foil with X1,Y1 mathematic plane). The intensity of the thus-created light trace or image is proportional to the radiation intensity of the respective point-source. The same situation occurs with the other points along the light source. Summing up contributions of all points of the elongated source in the observation plane yields a source image. This image is rotated at 1800 in its plane in relation to the original. In general, the brightness of the output image is proportional to the diameter of the δ hole. However, in this case, half-shadow effects are expressed more intensively. The image becomes blurred with the transition section size approximately equals 2δ. As the δ hole grows smaller, the intensity of image illumination decreases proportionally to the area of the hole and the sharpness of the image improve. However, this only occurs up to a certain limit. As the hole grows yet smaller, sharpness of picture decreases due to diffraction phenomena at the hole edges, causing growth of the transition section inversely to δ.

If a lens with focal distance equaling F is placed between the elongated light source and the foil in such a way that a light source is located in the lens focal plane, and the foil is illuminated with parallel beams from different points along the source, such a system turns out to have a much higher effective aperture as compared to a lensless system. If the source length is $D_1$, and the defect is shaped like a narrow slot $D_2$ in length positioned parallel to the source and sharing a common axis with it, and if $D_1$ exceeds $D_2$ significantly, the profile of the defect output-image will be trapezoidal. The half-shade size will equal $D_2$ in this case, and the size of the homogeneous section (trapezoid top base) equaling $D\Delta=D_1-D_2$. The image total size equals $D\Sigma=D_1+D_2$. In this case, we will obtain a sharper image of the defect in comparison with a lensless source. However, the size of the image greatly exceeds that of the defect.

Figure 3:
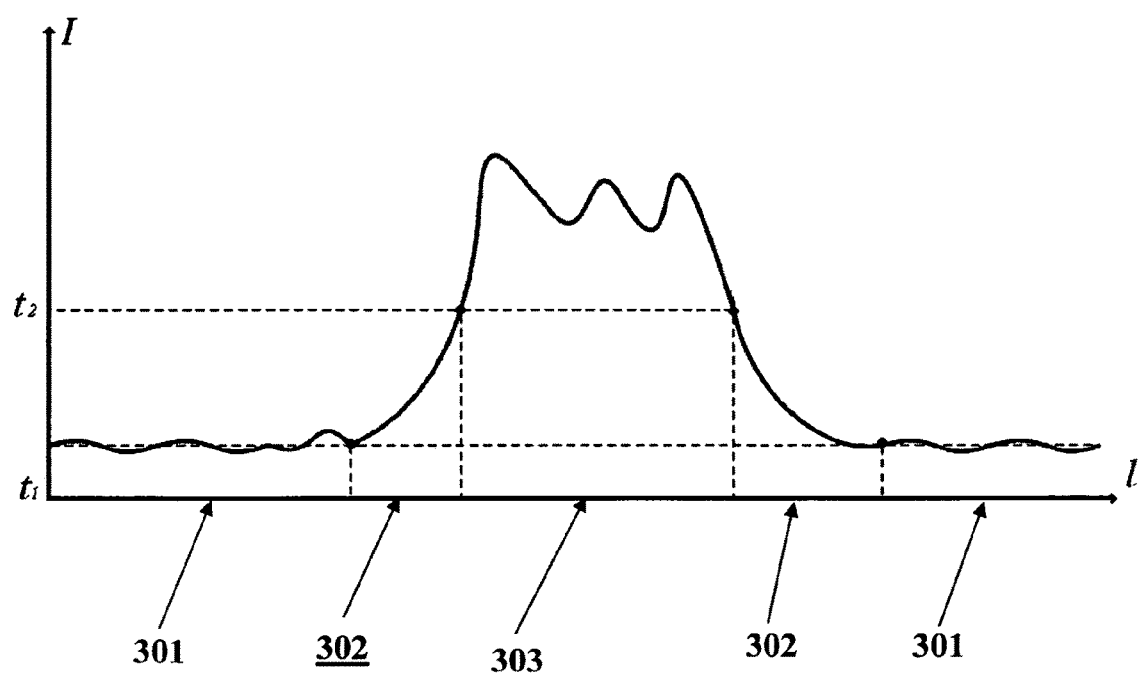
FIG. 3 represents the distribution of brightness along the image line that cross light from the defect. 301 is the area with the background of light; 302 is the area with the penumbra of light; 303 is the area with the light spot of defect.

To correct the effect of half-shadow in the general set of secondary-image elementary sections of the defect light spot, elementary sections are selected for which the brightness is greater than the second given threshold $t_2$ (see FIG. 3). The area of the light-spots outlines is determined. The light spots consists of the image elementary sections with brightness greater than the second given threshold and which have a common boundary.

Due to the fact that through-penetrating defects usually have a complex shape, an image of this defect contains, along with the basic light spot, several complex-configuration light spots located on the basic light spot's periphery and separated from the spot by half-shadow sections in some cases This is attributed, first of all, to the diffraction phenomenon at defect boundaries (edges). Therefore, in order to determine geometric dimensions of a pinhole or other through-penetrating defect, the light spot with the maximum area size is selected. The outline of this spot is approximated using a third-power polynomial at most and then the area of the approximated spot is determined.

Experiments demonstrate that brightness changes within the basic light spot, sometimes quite significantly. This is shown in FIG. 3. Therefore, brightness within the approximated outline of the basic light spot is averaged. Then the value of the spot average brightness is compensated by subtracting background brightness from it.

The generalized index of the defect light-spot secondary image is determined by multiplying its compensated brightness by the area of the approximated outline of the spot. The generalized index resulting value for defect optical size is determined by summing up the generalized indices of the initial and secondary image of the defect using the appropriate weighting coefficients. The weighting coefficient for the generalized index of the defect image is determined by dividing the number of elementary sections making up the given image by the total number of elementary sections making up the initial and secondary images of the defect.

The metric dimensions of a through-penetrating defect in the foil are determined by results of comparison of the resulting value of the defect optical-size generalized index with calibration data. The calibration data is obtained by processing images for artificial holes in the examined material, as described above. Artificial holes in metal foil are made using specially produced high-hardness metal needles or needles made of specially treated metal. In this process, foil is placed on hard metal substrate and pressed against it. Dimensions of the holes obtained in this way are determined by means of microscopic measurements or by means of micrometric measurements of needle thickness at a point that is one foil thickness away from needle's end.

The following examples illustrate present invention.

EXAMPLES

The Examples described below are provided for illustration purposes only and are not intended to limit the scope of the invention.

Example 1

The first example involves images of artificial defects in foil that were made by piercing the foil with metal needles. A halogen lamp with a 35 mm filament served as a light source. The distance from the filament to foil surface was 40 mm. A 10 micron thick titanium foil was used.

Figure 4:
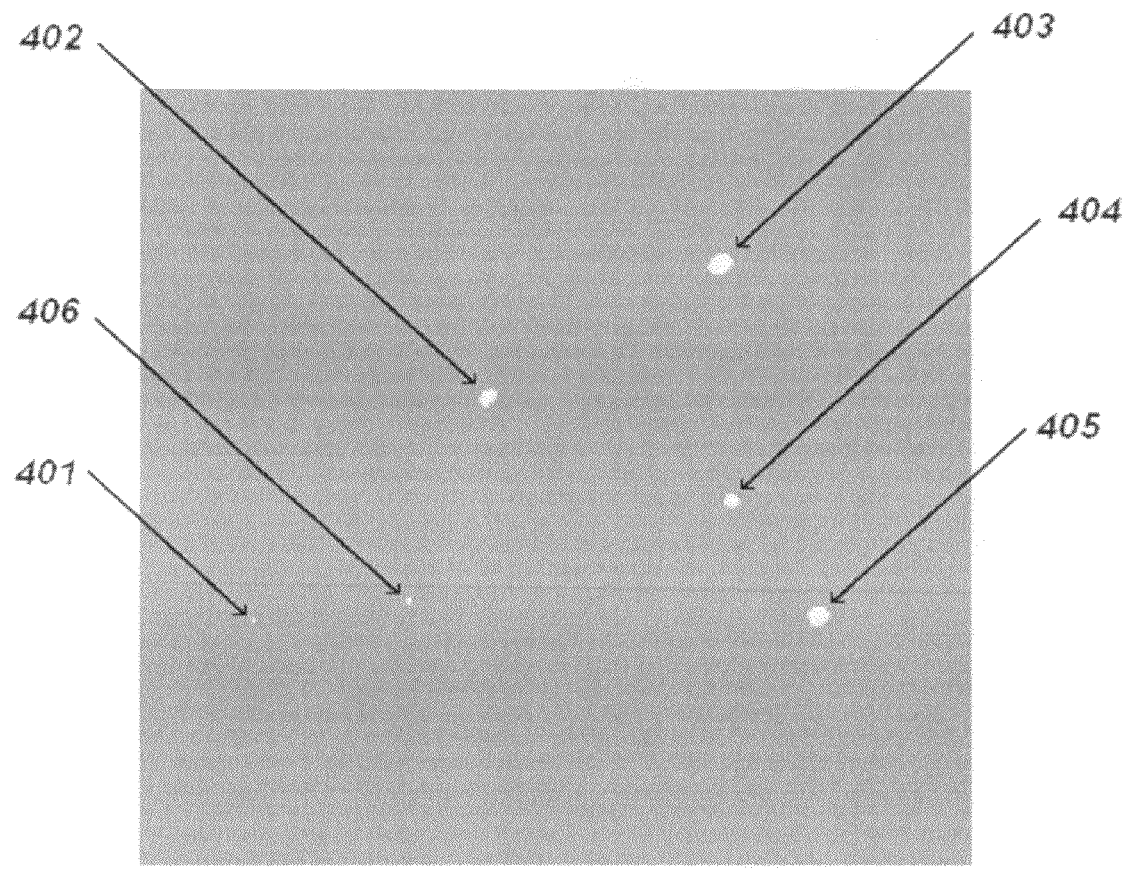
FIG. 4 represents the image of a group of artificial defects in a metal foil. Elements 401 and 406 show defect light spots with average diameter which is approximately equal to 20-30 microns; 402, 404, and 405 show defect light spots with an average diameter that is approximately equal to 50-70 microns; 403 shows a light spot defect with an average diameter equal to approximately 100 microns.

An Olympus SP-350 digital camera with resolution of 3264×2448 pixels was used as a registration gauge. Image capture was done from the distance of 50 mm from foil surface. The obtained image is shown in FIG. 4. Here the light spots from the defects are marked with numbers. The diameter of defect 1 is approximately 20 microns. The diameter of the largest defect (defect 3) is approximately 100 microns. As can be seen from the picture in FIG. 4, the light spot from defect 1 is much less bright than those from defects 2, 3, 4, and 5.

Example 2

In Example 2, the illumination conditions are the same as in Example 1. The same foil sample having the same defects was used. The distance between the foil and the image capture camera was increased to 100 mm. The scale of the obtained image was selected in such a way that the distance between the centers of the light spots was the same as in FIG. 4. An increased size of the spots was observed. The respective η coefficients for the increase in light spots' average diameters are listed in Table 1 below.

TABLE 1

The value of η factor for artificial defects.

| | Defect number | | | | | |
|---|---|---|---|---|---|---|
| | 1 | 2 | 3 | 4 | 5 | 6 |
| Expansion coefficient, η | 2.50 | 1.36 | 1.25 | 1.40 | 1.42 | 2.56 |

Results from the data in Table 1 show that as the distances between foil surface and the image capture camera are doubled, the light spot average diameter increases in different ways depending on the dimensions of the defect. Thus, for defects 1 and 6 that are approximately the same in size (20-30 microns), the η factor is about 2.5.

For defects 2, 4 and 5, with average diameter in the range 50-70 mm, the η factor's average value amounts to 1.4. For defect 3, the largest defect, the average diameter of which is approximately 100 microns, the η value is 1.25.

CLOSURE

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for detecting and evaluating defects that completely penetrate through a foil or film, said method comprising the steps of:

passing a flat foil or film between at least one optical image capture device and at least one elongated light source comprising an infinite number of point sources that are not in phase and are emitting light independently from one another, wherein said optical image capture device is positioned on one side a first surface of said foil and at a first distance from said first surface and said elongated light source is positioned on a second opposite side of said of said foil or film;

periodically capturing automatic computer-controlled image of the foil surface with said image capture device to produce at least a first image;

transmitting said at least first image to a control computer;

processing the transmitted first image to detect whether a first light spot image associated with a defect is present and, if present, determining the brightness and area of the first light spot of said first light spot image;

calculating a first generalized index of said first image by multiplying said brightness and said area of said first light spot image;

stopping the movement of a foil or film upon detection of said first light spot image;

moving the image capture device to a second distance from the foil or film surface;

repositioning said image capture device in the plane parallel to foil or film surface;

stopping said image capture device when the light spot of said defect comes into the focus;

automatically capturing a second image;

transmitting said second image to said computer;

processing said second image to form a second light spot image determining the brightness and area of the second light spot of said second light spot image;

calculating a second generalized index of said second image by multiplying said brightness and said area of said second light spot image;

calculating a third generalized index using said first and second generalized indices; and evaluating the dimensions of said through-penetrating defect in said foil or film by comparing the third generalized index with calibrated generalized indices.

2. The method of claim 1 wherein said third generalized index is calculated by adding said first and second generalized indices.

3. The method of claim 2 wherein said first and said second indices are multiplied by a weighing coefficient before said adding.

4. The method of claim 3 wherein said weighing coefficient for said first generalized index is determined by dividing the number of elementary sections making up the first image by the total number of elementary sections making up the first and second images of the defect and said weighing coefficient for said second generalized index is determined by dividing the number of elementary sections making up the second image by the total number of elementary sections making up the first and second images.

5. The method of claim 1 wherein said processing of said first image comprises selecting image elementary sections which are brighter than a given level; determining the initial outline area of the light spot comprising said selected elementary sections having a common boundary; determining the first generalized index; and reporting the presence of a defect if said first generalized index value exceeds a preset threshold value.

6. The method of claim 1 wherein said processing of said second image comprises:

determining an average background brightness of elementary sections of the second image with a brightness less than a first threshold, selecting image elementary sections which are brighter than a second threshold and which have a common boundary;

selecting the light spot with the greatest area;

approximating the selected light spot with a third order polynomial;

determining the area of the approximated light spot;

determining the brightness of the approximated light spot;

subtracting the average brightness background from the brightness of the approximated light spot to produce a compensated brightness; and determining the second generalized index by multiplying the compensated brightness by the area of the approximated light spot.

7. The method according to claim 1, wherein calibration data is obtained by processing images for artificial holes in foil or film, said hole dimensions being determined by means of microscopic measurements or by means of micrometric measurements of the size of the tool used to produce the artificial holes.

8. Apparatus for optical detection and size evaluation of defects that penetrate completely through a moving foil or film, said apparatus comprising, at least one image capture device and at least one elongated light source comprising an infinite number of point sources that are not in phase and are which emit light independently from one another, wherein said optical image capture device is positioned so as to be on one side a first surface of a foil or film, when present in said apparatus, and at a first distance from said first surface and said elongated light source is positioned on a second opposite side of said of said foil or film, when present in said apparatus;

transportation means for moving the image capture device along a line normal to the surface of the foil or film;

transportation means for moving the image capture device in a plane parallel to the surface of the foil or film;

means of stopping the movement of the foil or film; and a computer comprising (i) at least one processor, (ii) a memory, and (iii) at least one program, wherein the at least one program is stored in the memory and executable by the at least one processor, the at least one program comprising instructions to control:

the passing of a flat foil or film between the at least one optical image capture device and the at least one elongated light source, the periodic capturing of images of the foil surface with said image capture device to produce at least a first image;

the transmission of said at least first image to the computer;

the processing of the transmitted first image to detect whether a first light spot image associated with a defect is present and, if present, determining the brightness and area of the first light spot of said first light spot image;

the calculating of a first generalized index of said first image by multiplying said brightness and said area of said first light spot image;

the stopping of the movement of a foil or film upon detection of said first light spot image;

the moving of the image capture device to a second distance from the foil or film surface;

the repositioning of the image capture device in the plane parallel to foil or film surface;

the stopping of the image capture device when the light spot of said defect comes into the focus;

the automatic capturing of a second image the transmission of said second image to said computer;

the processing of said second image to form a second light spot image determining the brightness and area of the second light spot of said second light spot image;

the calculating of a second generalized index of said second image by multiplying said brightness and said area of said second light spot image;

the calculating of a third generalized index using said first and second generalized indices; and the evaluation of the dimensions of said through defect in said foil or film by comparing the third generalized index with calibrated generalized indices.

9. The apparatus according to claim 8, wherein the axis of symmetry of the objective lens of each image capture device positioned at the first given distance from the foil surface is perpendicular to this surface and cross the surface on a line that is parallel to the foil or film side edges and located at an equal distance from said edges.

10. The apparatus according to claim 8, wherein the distance between the axes of symmetry of the objective lenses of the image capture devices is determined by the given surface-section area of the foil or film captured by means of an image capture device, by the foil or film speed of movement and by the minimal time span between two consecutive automatic-mode image capture cycles.

11. The apparatus according to claim 10, wherein the minimal time span between two consecutive automatic-mode image capture cycles is determined by the time interval required for computer-controlled image capture and the time interval required for transmission of the image captured by the image capture device to the computer.

12. The apparatus according to claim 8, wherein an elongated light source is oriented in such a way that its axis is perpendicular to the direction of the foil or film movement.

13. The apparatus according to claim 8, wherein the means for transporting the image capture devices, stopping the foil band movement, as well as the defect-marking means, all have interfaces for communication with the control computer.

14. The apparatus of claim 8 further comprising means for marking the location of a defect on the surface of the foil.

* * * * *